(12) United States Patent
Tanaka et al.

(10) Patent No.: US 12,203,012 B2
(45) Date of Patent: Jan. 21, 2025

(54) STRATUM CORNEUM-COLLECTING ADHESIVE COMPOSITION, STRATUM CORNEUM-COLLECTING INSTRUMENT, BIOLOGICAL SUBSTANCE EXTRACTION KIT, AND BIOLOGICAL SUBSTANCE COLLECTION METHOD

(71) Applicant: Shiseido Company, Ltd., Tokyo (JP)

(72) Inventors: Chika Tanaka, Tokyo (JP); Tomoko Onodera, Tokyo (JP); Masaya Takagi, Tokyo (JP); Chieko Mizumoto, Tokyo (JP); Daisuke Kubota, Shiga (JP); Masahiko Yano, Shiga (JP)

(73) Assignee: Shiseido Company, Ltd., Tokyo (JP)

( * ) Notice: Subject to any disclaimer, the term of this patent is extended or adjusted under 35 U.S.C. 154(b) by 1105 days.

(21) Appl. No.: 17/055,310

(22) PCT Filed: May 14, 2019

(86) PCT No.: PCT/JP2019/019050
§ 371 (c)(1),
(2) Date: Nov. 13, 2020

(87) PCT Pub. No.: WO2019/221099
PCT Pub. Date: Nov. 21, 2019

(65) Prior Publication Data
US 2021/0179905 A1 Jun. 17, 2021

(30) Foreign Application Priority Data
May 17, 2018 (JP) .................. 2018-095589

(51) Int. Cl.
| | | |
|---|---|---|
| *C09J 193/04* | (2006.01) | |
| *A61B 10/02* | (2006.01) | |
| *C09J 11/06* | (2006.01) | |
| *C09J 11/08* | (2006.01) | |
| *G01N 1/04* | (2006.01) | |

(Continued)

(52) U.S. Cl.
CPC ............. *C09J 193/04* (2013.01); *A61B 10/02* (2013.01); *C09J 11/06* (2013.01); *C09J 11/08* (2013.01); *G01N 1/04* (2013.01); *G01N 1/4055* (2013.01); *G01N 2001/085* (2013.01); *G01N 2001/4061* (2013.01)

(58) Field of Classification Search
None
See application file for complete search history.

(56) References Cited

U.S. PATENT DOCUMENTS

2006/0155025 A1* 7/2006 Arai .................. C09J 11/06
524/310
2008/0022226 A1* 1/2008 Brown ................ G06F 3/0484
715/825

(Continued)

FOREIGN PATENT DOCUMENTS

CN 1856559 A 11/2006
JP 07076518 A * 3/1995

(Continued)

*Primary Examiner* — Peter A Salamon
(74) *Attorney, Agent, or Firm* — Foley & Lardner LLP

(57) ABSTRACT

A stratum corneum-collecting adhesive composition includes a hydrophobic component having adhesiveness, and a hydrophilic component that is present in a dispersed state in the hydrophobic component.

15 Claims, 9 Drawing Sheets

(51) Int. Cl.
*G01N 1/40* (2006.01)
*G01N 1/08* (2006.01)

(56) References Cited

U.S. PATENT DOCUMENTS

| | | | |
|---|---|---|---|
| 2008/0033336 A1* | 2/2008 | Sangha | A61B 10/02 604/1 |
| 2008/0125743 A1* | 5/2008 | Yuzhakov | A61M 37/0015 604/506 |
| 2010/0254581 A1 | 10/2010 | Neeser et al. | |
| 2012/0150004 A1* | 6/2012 | Currie | A61B 5/157 600/347 |
| 2013/0123595 A1* | 5/2013 | Currie | A61B 5/150358 600/347 |
| 2013/0144142 A1* | 6/2013 | Vidalis | A61B 5/14514 600/347 |
| 2014/0275895 A1* | 9/2014 | Vidalis | A61B 5/150076 156/247 |
| 2018/0340866 A1 | 11/2018 | Takata et al. | |

FOREIGN PATENT DOCUMENTS

| | | |
|---|---|---|
| JP | 2000-044476 A | 2/2000 |
| JP | 2004-053491 A | 2/2004 |
| JP | 2007-003413 A | 1/2007 |
| JP | 2015-001476 A | 1/2015 |
| JP | 2015-175617 A | 10/2015 |
| JP | 2016-075640 A | 5/2016 |
| WO | WO-2017/077562 A1 | 5/2017 |

* cited by examiner

[Fig. 1]
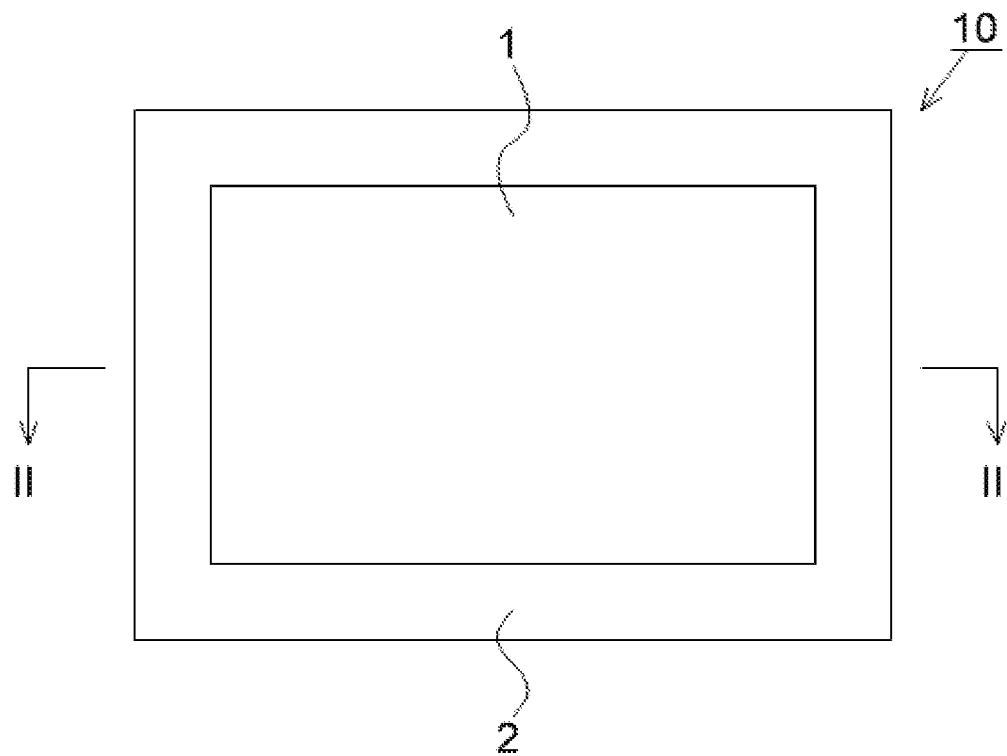
[Fig. 2]
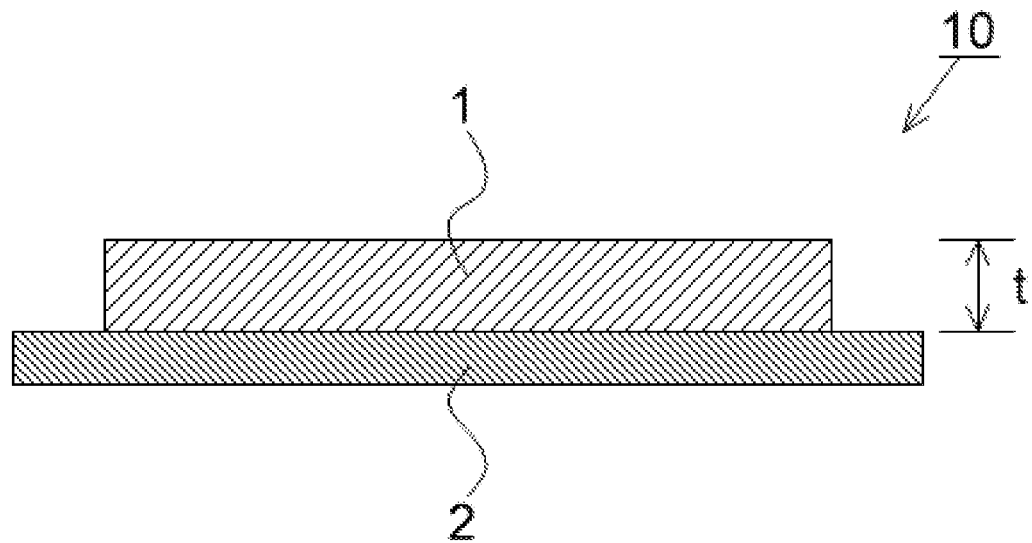

[Fig. 3]
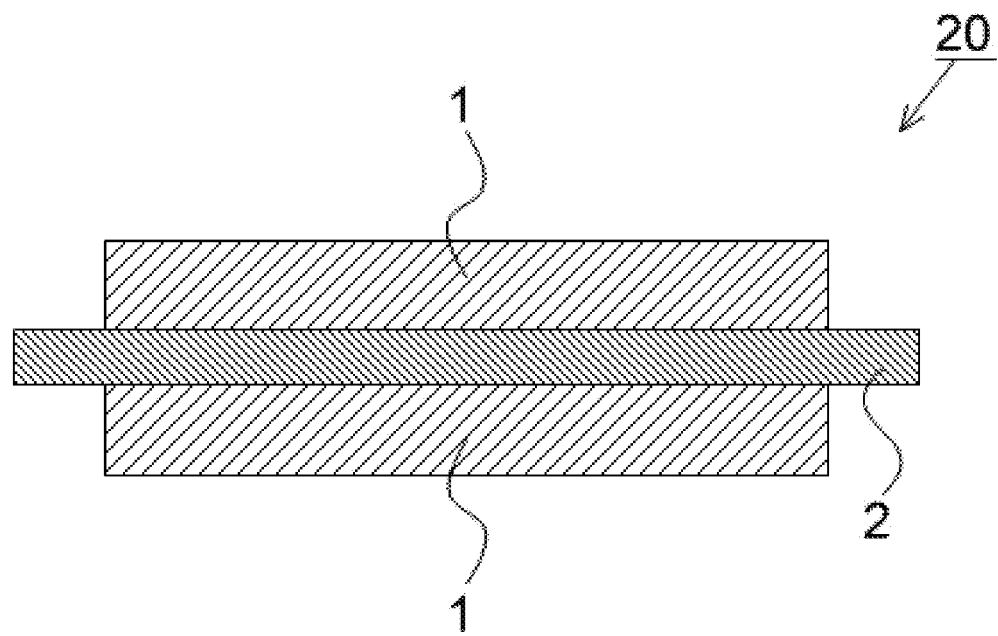

[Fig. 4]
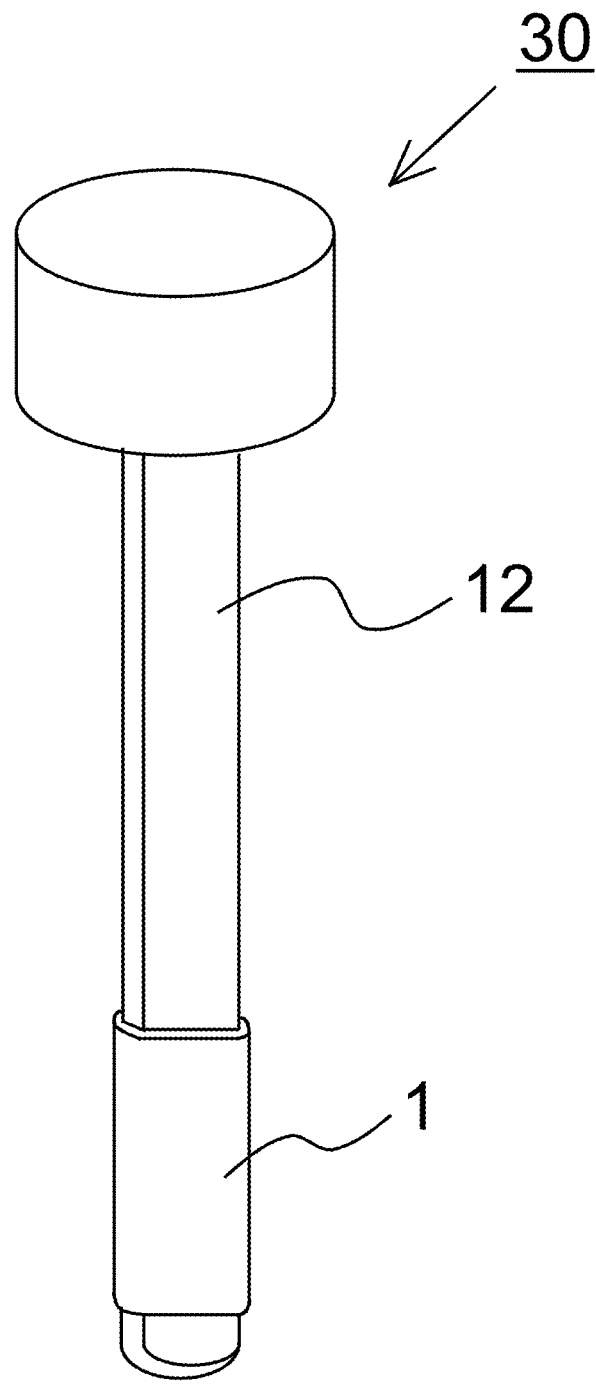

[Fig. 5]
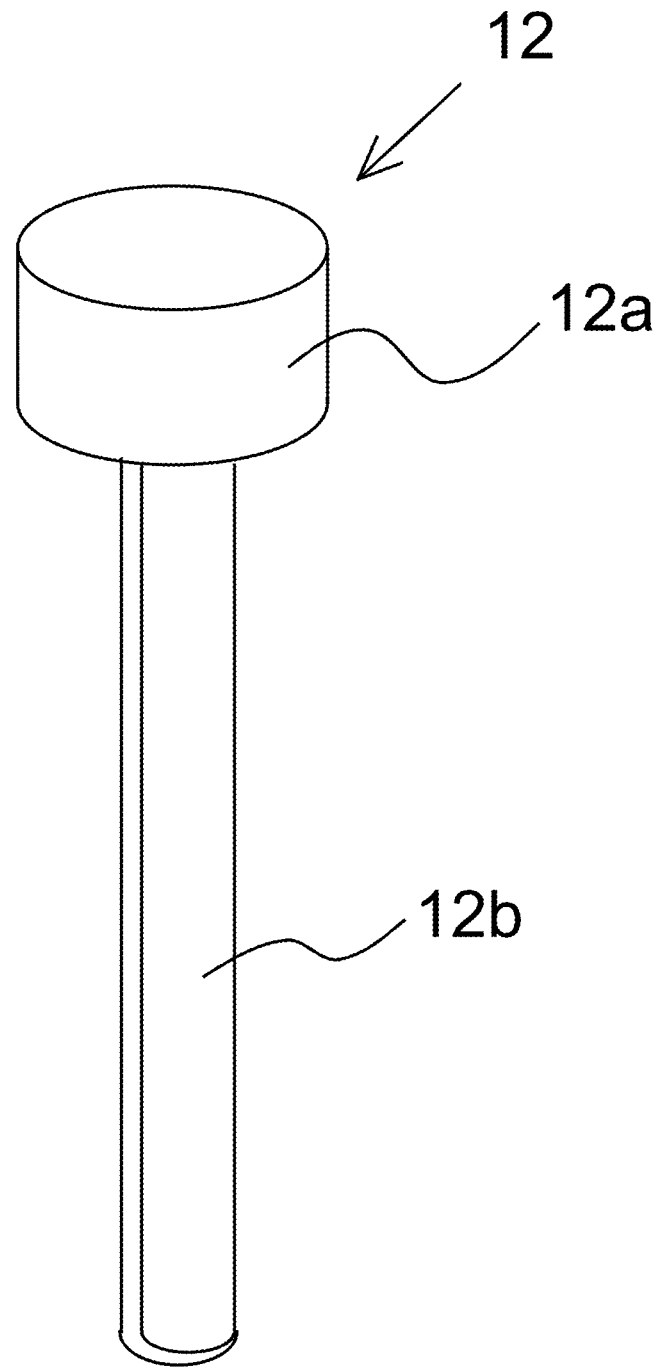

[Fig. 6]
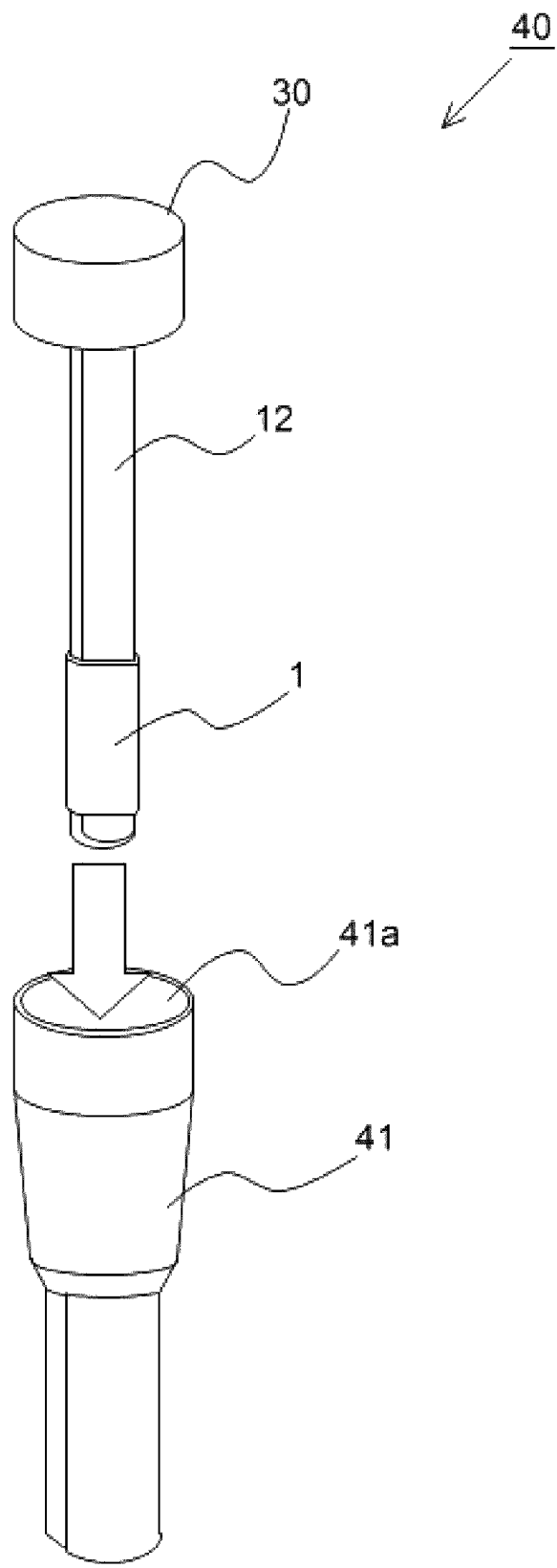

[Fig. 7]
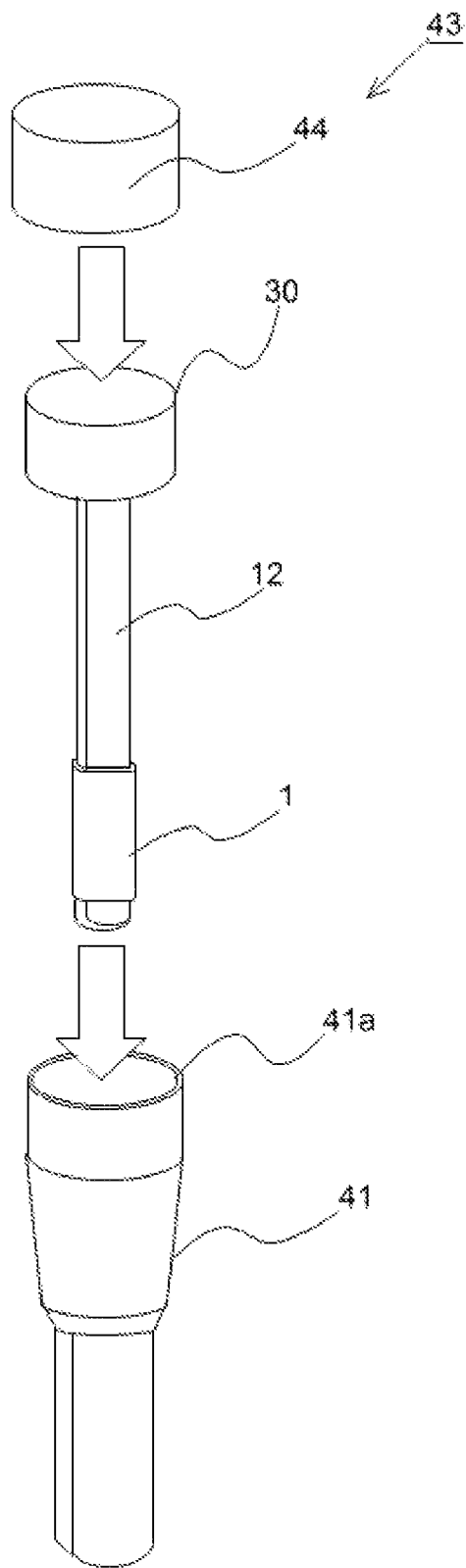

[Fig. 8]
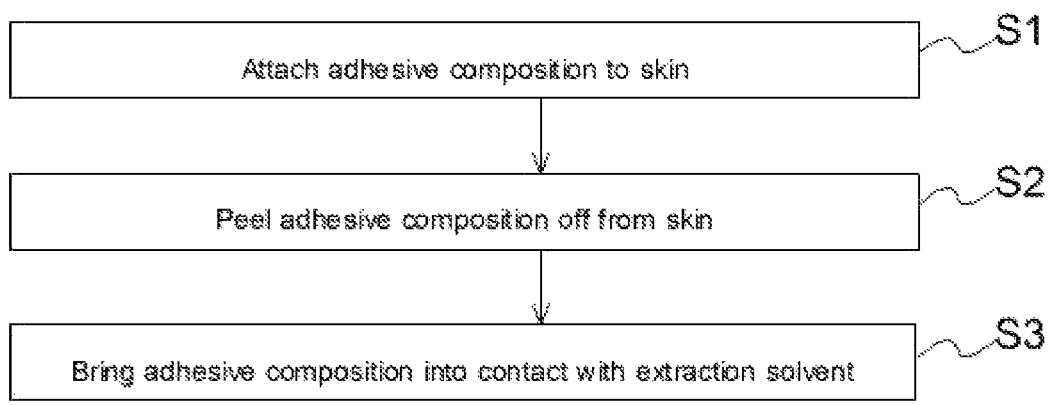

[Fig. 9]
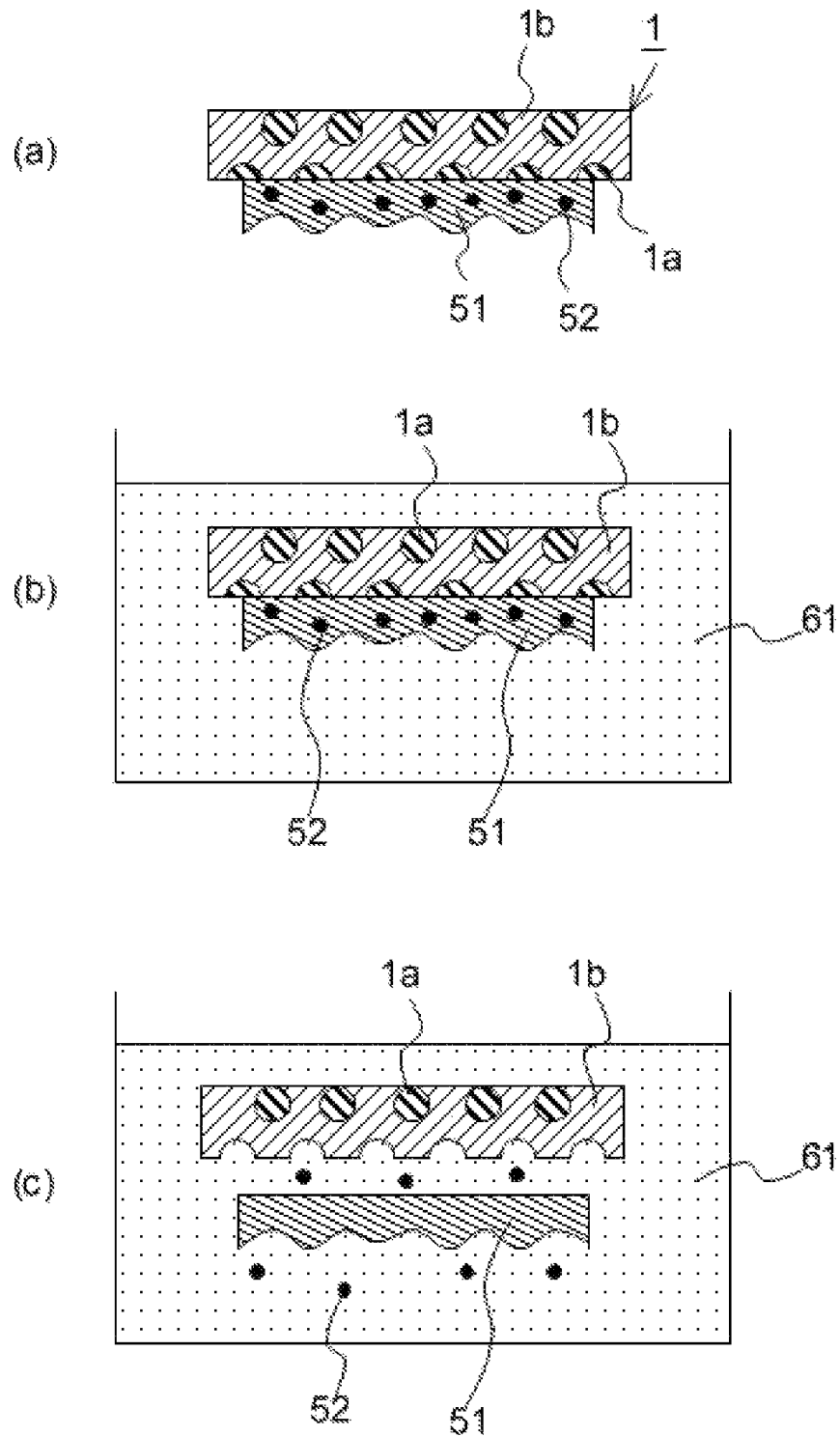

[Fig. 10]
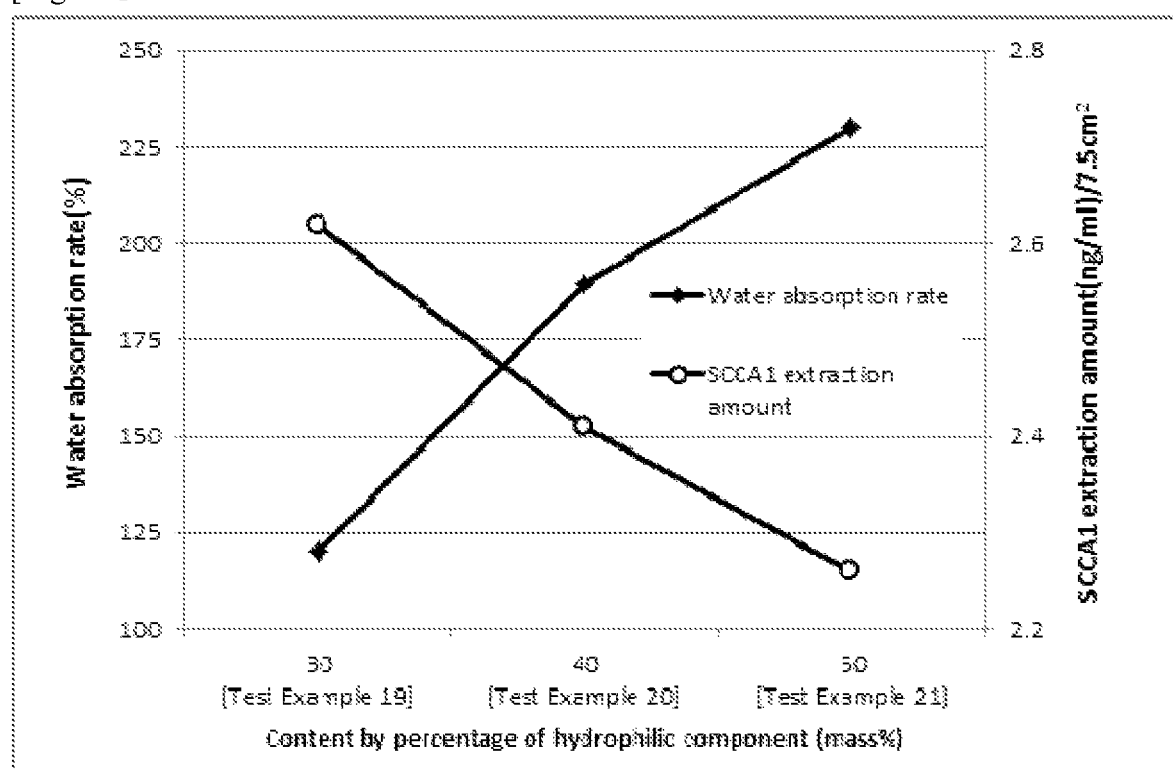

STRATUM CORNEUM-COLLECTING ADHESIVE COMPOSITION, STRATUM CORNEUM-COLLECTING INSTRUMENT, BIOLOGICAL SUBSTANCE EXTRACTION KIT, AND BIOLOGICAL SUBSTANCE COLLECTION METHOD

CROSS-REFERENCE TO RELATED APPLICATIONS

This application is the U.S. National Stage of PCT/JP2019/019050, filed May 14, 2019, which claims priority to JP 2018-095589, filed May 17, 2018.

TECHNICAL FIELD

The present disclosure relates to a stratum corneum-collecting adhesive composition. The present disclosure relates to a stratum corneum-collecting instrument including the adhesive composition. The present disclosure relates to a biological substance extraction kit including the stratum corneum-collecting instrument. The present disclosure relates to a method for extracting a biological substance contained in the stratum corneum.

BACKGROUND ART

There are methods for determining the state of the skin on the basis of biological substances, such as proteins, contained in the stratum corneum. The state of the skin can be determined, for example, according to the following process. First, the stratum corneum is collected from the skin by using an adhesive. Next, a biological substance is extracted into a solvent from the stratum corneum adhering to the adhesive. Then, the type and amount of the biological substance contained in the extraction solvent are measured, to determine the state of the skin on the basis of the measurement result.

For example, Patent Literature 1 discloses a stratum corneum-collecting instrument for collecting the stratum corneum of the skin, and a stratum corneum collecting/detecting kit for detecting a specific component from the stratum corneum of the skin. The stratum corneum collecting/detecting kit disclosed in Patent Literature 1 includes: a stratum corneum-collecting instrument including a rod shaped portion having a grip portion at one end to be gripped by a user, a columnar portion which is continuous with the other end of the rod shaped portion, and an adhesive layer formed on a circumferential surface of the columnar portion; a solvent container, which is a bottomed cylindrical container having an opening in an upper portion thereof, containing a solvent for extracting a component from stratum corneum collected by the adhesive layer, the solvent container receiving the columnar portion of the stratum corneum-collecting instrument through the opening so as to enable the adhesive layer to be immersed in the solvent; and a lid for closing the opening of the solvent container after the adhesive layer is immersed in the solvent.

CITATION LIST

Patent Literature

Patent Literature 1: Japanese Unexamined Patent Publication No. 2016-75640A

SUMMARY OF INVENTION

Technical Problem

For example, in the stratum corneum collecting/detecting kit disclosed in Patent Literature 1, the stratum corneum adhering to the adhesive is immersed in the extraction solvent contained in the container, to extract a biological substance. In such cases, the ease of extracting the biological substance depends on the adhesive. Unfortunately, adhesives used heretofore do not allow biological substances to be extracted sufficiently simply by immersing the stratum corneum adhering to an adhesive into an extraction solvent. Therefore, various improvements in the adhesive are necessary to actually use the stratum corneum-collecting instrument and the stratum corneum collecting/detecting kit disclosed in Patent Literature 1. Conventional adhesives require a multitude of steps, such as the following, to extract a biological substance from the stratum corneum adhering to the adhesive.

Consider, for example, a case of using cellophane tape, which is a type of stationery coated with a rubber-based adhesive, as an instrument for collecting stratum corneum. In such cases, the extraction of a biological substance requires the following steps: attaching the cellophane tape to the skin; making the stratum corneum adhere to the cellophane tape by peeling the cellophane tape from the skin; cutting up the stratum corneum-adhering cellophane tape into a plurality of fine pieces to be placeable in a centrifuge tube; placing each piece of cut tape into a centrifuge tube containing an extraction solvent; placing each tube in an ultrasonic homogenizer to subject the extraction solution, in which the tape is immersed, to an ultrasonic treatment; then placing each tube in a centrifugal separator to subject the extraction solution to centrifugal separation; and finally collecting the extraction solution from each tube and measuring the desired biological substance. This series of tasks requires much time and effort, as well as a large-scale device.

There has thus been a demand for a technique that enables a desired amount of biological substance to be extracted easily and quickly from the stratum corneum adhering to an adhesive.

Solution to Problem

According to a first aspect of the present disclosure, a stratum corneum-collecting adhesive composition is provided, the adhesive composition comprising a hydrophobic component having adhesiveness; and a hydrophilic component that is present in a dispersed state in the hydrophobic component.

According to a second aspect of the present disclosure, a stratum corneum-collecting instrument is provided, the instrument comprising the adhesive composition according to the first aspect; and a support having the adhesive composition provided to at least a portion thereof.

According to a third aspect of the present disclosure, a biological substance extraction kit is provided, the kit comprising the stratum corneum-collecting instrument according to the second aspect; and a container that has an opening, and that is configured to receive the adhesive composition through the opening.

According to a fourth aspect of the present disclosure, a biological substance extraction method is provided, the method comprising a collection step of attaching the adhesive composition according to the first aspect to the skin, and causing stratum corneum to adhere to the adhesive composition; and an extraction step of bringing at least a portion of the adhesive composition, to which the stratum corneum has adhered, into contact with a solvent, and extracting a biological substance from the stratum corneum into the solvent.

Advantageous Effects of Invention

With the stratum corneum-collecting adhesive composition and the stratum corneum-collecting instrument according to the present disclosure, it is possible to collect a sufficient amount of stratum corneum from the skin of a subject, without placing any burden on the subject's skin.

With the stratum corneum-collecting adhesive composition, the biological substance extraction kit, and the biological substance collection method according to the present disclosure, it is possible to extract a biological substance from the stratum corneum adhering to the adhesive composition easily and in a short time.

BRIEF DESCRIPTION OF DRAWINGS

FIG. 1 is a schematic plan view of a stratum corneum-collecting instrument according to a first mode of a second embodiment.

FIG. 2 is a schematic cross-sectional view of the stratum corneum-collecting instrument taken along line II-II in FIG. 1.

FIG. 3 is a schematic cross-sectional view of a stratum corneum-collecting instrument having a different form from FIG. 1.

FIG. 4 is a schematic perspective view of a stratum corneum-collecting instrument according to a second mode of the second embodiment.

FIG. 5 is a schematic perspective view of a support according to the second mode of the second embodiment.

FIG. 6 is a schematic perspective view of a biological substance extraction kit according to a third embodiment.

FIG. 7 is a schematic perspective view of a biological substance extraction kit having a different form from that illustrated in FIG. 6.

FIG. 8 is a flowchart of a biological substance collection method according to a fourth embodiment.

FIG. 9 is a conceptual diagram for illustrating a principle behind the biological substance collection method.

FIG. 10 is a graph illustrating a relationship among the content by percentage of the hydrophilic component, the water absorption rate, and SCCA1 extraction amount in Test Examples 19 to 21.

DESCRIPTION OF EMBODIMENTS

Preferred modes of the aforementioned aspects are described below.

According to a preferred mode of the above first aspect, a content by percentage of the hydrophilic component is from 10 to 60% by mass to a mass of the adhesive composition.

According to a preferred mode of the above first aspect, a content by percentage of the hydrophobic component is from 40 to 90% by mass to the mass of the adhesive composition.

According to a preferred mode of the above first aspect, the hydrophobic component contains a tackifier in an amount of from 10 to 50% by mass to the mass of the adhesive composition; and a shape retention agent in an amount of from 5 to 50% by mass to the mass of the adhesive composition.

According to a preferred mode of the above first aspect, the tackifier contains at least one selected from the group consisting of rosin-based resins, terpene-based resins, and alicyclic hydrocarbon resins.

According to a preferred mode of the above first aspect, the shape retention agent contains at least one selected from the group consisting of polyisobutylene, styrene/isobutylene/styrene copolymer, and styrene/butylene/styrene copolymer.

According to a preferred mode of the above first aspect, the hydrophobic component further contains a softener in an amount of from 3 to 20% by mass to the mass of the adhesive composition.

According to a preferred mode of the above first aspect, the softener contains at least one selected from the group consisting of liquid paraffin, polybutene, lanolin, vegetable oils, carboxylic acid compounds, and ester compounds.

According to a preferred mode of the above first aspect, the hydrophilic component contains at least one selected from the group consisting of water-soluble carboxymethyl cellulose and salts thereof, water-insoluble carboxymethyl cellulose and salts thereof, alginic acid and salts thereof, vinyl acetate/vinylpyrrolidone copolymer, polyvinylpyrrolidone, and polyvinylpolypyrrolidone.

According to a preferred mode of the above first aspect, the adhesive composition has a water absorption rate of 200% or less.

According to a preferred mode of the above first aspect, the adhesive composition further comprises a surfactant in an amount of 5% by mass or less to the mass of the adhesive composition.

According to a preferred mode of the above first aspect, the surfactant is a hydrophilic nonionic surfactant.

According to a preferred mode of the above first aspect, the adhesive composition is for collecting a biological substance in the stratum corneum.

According to a preferred mode of the above first aspect, the biological substance is a protein.

According to a preferred mode of the above first aspect, the biological substance is at least one selected from the group consisting of SCCA1, SOD1, SOD2, IL-1ra, IL-1α, IL-1β, MMP9, MMP2, AZGP1, cathepsins, S100 protein, VEGF, KLK-5, KLK-7, KLK-8, KLK-11, KLK-12, KLK-13, elafin, TACE, and CALML-5.

According to a preferred mode of the above second aspect, the support is a sheet.

According to a preferred mode of the above second aspect, the support includes a grip portion to be held by a user, and a stratum corneum-collecting portion extending from the grip portion. The adhesive composition is provided to at least a portion of the stratum corneum-collecting portion.

According to a preferred mode of the above second aspect, the stratum corneum-collecting portion has a columnar or rod-like shape. The adhesive composition is provided on a tip-end side which is on an opposite side from the grip portion.

According to a preferred mode of the above third aspect, the stratum corneum-collecting instrument is attachable to the container in a manner that a liquid inside the container does not spill out.

According to a preferred mode of the above third aspect, in the extraction step, the solvent is shaken while keeping the adhesive composition in contact with the solvent.

According to a preferred mode of the above third aspect, the solvent is a solution containing a buffer and a nonionic surfactant.

In the description below, the reference signs in the drawings are provided for the sake of understanding of the invention, and are not intended to limit the invention to the forms/modes illustrated in the drawings. Further, the invention is not to be limited to the shapes, dimensions, scale, etc. illustrated in the drawings. In the various embodiments, the same elements are respectively accompanied by the same reference signs.

In the following description, POE is an abbreviation of polyoxyethylene, and POP is an abbreviation of polyoxypropylene. The number in parentheses after POE or POP indicates the average number of moles of POE groups or POP groups added in the compound in question.

An adhesive composition according to a first embodiment of the present disclosure will be described. The adhesive composition of the present disclosure can be used to collect the stratum corneum from the skin (human skin).

The adhesive composition of the present disclosure contains a hydrophobic component and a hydrophilic component. The hydrophobic component may contain, for example, a tackifier (an agent that imparts adhesiveness), a shape retention agent (excipient), and/or a softener (plasticizer). In the adhesive composition, the hydrophobic component is preferably a continuous phase.

Hydrophobic Components:
Tackifier:

The adhesive composition may contain a tackifier. It is preferred that the tackifier is capable of causing adhesion of the stratum corneum without deeply damaging the skin, or without causing strong pain to a subject, when brought into contact with the skin. For the tackifier, it is possible to use, for example, known tackifiers usable in adhesive skin patches. For the tackifier, it is possible to use, for example, at least one selected from rosin-based resins, terpene-based resins, alicyclic hydrocarbon resins, and rubber-based resins. The tackifier preferably contains a polar group and/or a polar bond, such as a hydroxy group, a carboxy group, an ester bond, and/or an ether bond, to enhance affinity to the skin and the extraction solvent while maintaining hydrophobicity.

Examples of usable rosin-based resins may include rosin esters, such as ester derivatives of rosin acid. The rosin ester may be, for example, an ester compound between rosin acid and a polyol. Rosin esters may encompass hydrogenated rosin esters. Examples of usable rosin-based resins include rosin glycerin ester, rosin pentaerythritol ester, hydrogenated rosin, hydrogenated rosin glycerin ester, and hydrogenated rosin pentaerythritol ester. An example of a usable commercial product of rosin ester includes Pine Crystal (registered trademark) KE-311 (from Arakawa Chemical Industries, Ltd.).

Examples of usable terpene-based resins may include aromatic-modified terpene polymers and terpene phenolic copolymers. An example of a usable commercial product of terpene-based resin includes YS Resin (from Yasuhara Chemical Co., Ltd.).

The content by percentage of the tackifier in the adhesive composition is preferably 10% by mass or greater, more preferably 15% by mass or greater, even more preferably 20% by mass or greater, relative to the mass of the adhesive composition. If the content by percentage of the tackifier is less than 10% by mass, sufficient adhesion of the stratum corneum cannot be achieved. The content by percentage of the tackifier may be 25% by mass or greater, 30% by mass or greater, or 35% by mass or greater, relative to the mass of the adhesive composition. The content by percentage of the tackifier is preferably 50% by mass or less, more preferably 45% by mass or less, relative to the mass of the adhesive composition. If the content by percentage of the tackifier exceeds 50% by mass, adhesive force may become too strong, and also cohesive failure may become likely.

Shape Retention Agent:

The adhesive composition may also contain a shape retention agent. The shape retention agent is preferably an agent that contributes to the shape retainability of the tackifier so as to suppress splitting of the adhesive composition, as well as adhesive residue, at the time of attaching or removing the adhesive composition. The shape retention agent is also preferably an agent that imparts, to the adhesive composition, resistance to extraction solvents for extracting biological substances. The shape retention agent may also impart, to the adhesive composition, properties such as adhesiveness, water resistance, softness, elasticity, and/or affinity to the skin. Examples of usable shape retention agents may include polyisoprene, polyisobutylene, styrene-isoprene-styrene (SIS) block copolymer, styrene-isoprene block copolymer, styrene-butadiene-styrene (SBS) copolymer, styrene-butadiene block copolymer, styrene-ethylene-butadiene-styrene block copolymer, styrene-butadiene-ethylene-styrene block copolymer, and isoprene rubber. In cases where the shape retention agent is a polymer, its molecular weight can be set as appropriate depending on the intended property. For example, when using polyisobutylene, the molecular weight of polyisobutylene may be 100,000 or less in cases where the adhesive composition is to be improved in softness and affinity to the skin; whereas, in cases where the adhesive composition is to be improved in strength and hardness, the molecular weight of polyisobutylene may exceed 100,000. When using SIS block copolymer, the SIS block copolymer may have a melt flow rate of, for example, from 1 to 65 g/10 minutes.

For example, the shape retention agent preferably contains SIS block copolymer and polyisobutylene. This can provide the adhesive composition with strength capable of withstanding use, good skin penetration, and resistance to extraction solvents. In this case, the content ratio may be, for example, at least 0.3 parts by mass, preferably at least 0.5 parts by mass, of polyisobutylene relative to 1 part by mass of SIS block copolymer. The content ratio may also be, for example, at most 2 parts by mass, preferably at most 1.8 parts by mass, of polyisobutylene relative to 1 part by mass of SIS block copolymer.

The content by percentage of the shape retention agent in the adhesive composition is preferably 5% by mass or greater, more preferably 10% by mass or greater, even more preferably 15% by mass or greater, relative to the mass of the adhesive composition. If the content by percentage of the shape retention agent is less than 5% by mass, the adhesive composition may lack cohesive force, which may result in adhesive residue when peeling the composition off from the skin. The content by percentage of the shape retention agent may also be 20% by mass or greater, 25% by mass or greater, or 30% by mass or greater, relative to the mass of the adhesive composition. The content by percentage of the shape retention agent is preferably 50% by mass or less, more preferably 40% by mass or less, relative to the mass of the adhesive composition. If the content by percentage of the shape retention agent exceeds 50% by mass, the adhesive composition may become stiff, which may impair adhesiveness.

Softener:

The adhesive composition may also contain a softener. The softener is preferably an agent that can make the shape retention agent soft. The softener can also achieve adhesiveness together with the tackifier, and allow the adhesive composition to be easily attached to, and/or removed from, the skin. The softener can also reduce the subject's pain when peeling the adhesive composition off from the skin. Examples of usable softeners may include lanolin, liquid paraffin, polybutylene, squalane, squalene, vegetable oils (castor oil, jojoba oil, olive oil, soybean oil, etc.), polybutene, aromatic dicarboxylic acids (phthalic acid, isophthalic acid, terephthalic acid, etc.), aliphatic dicarboxylic acids (succinic acid, glutaric acid, adipic acid, pimelic acid, suberic acid, azelaic acid, sebacic acid, etc.), fatty acid esters, dibasic acid esters, and polyesters.

The content by percentage of the softener in the adhesive composition is preferably 3% by mass or greater, more preferably 5% by mass or greater, relative to the mass of the adhesive composition. If the content by percentage of the softener is less than 3% by mass, the adhesive composition may become stiff, which may suppress adhesiveness. The content by percentage of the softener is preferably 20% by mass or less, more preferably 15% by mass or less, even more preferably 10% by mass or less, relative to the mass of the adhesive composition. If the content by percentage of the softener exceeds 20% by mass, the composition may become too soft, which may deteriorate adhesive force, and also, the cohesive force of the adhesive composition may deteriorate, which may cause cohesive failure.

Others:

The adhesive composition may further contain, as hydrophobic components, components other than tackifiers, shape retention agents, and softeners.

The content by percentage of the aforementioned hydrophobic component(s) is preferably 40% by mass or greater, more preferably 50% by mass or greater, even more preferably 60% by mass or greater, relative to the mass of the adhesive composition. If the content by percentage of the hydrophobic component(s) is less than 40% by mass, adhesive force may be insufficient, which may make it impossible to achieve collection of stratum corneum of the skin. The content by percentage of the hydrophobic component(s) is preferably 90% by mass or less, more preferably 80% by mass or less, even more preferably 70% by mass or greater, relative to the mass of the adhesive composition. If the content by percentage of the hydrophobic component(s) exceeds 90% by mass, it may become impossible to separate the collected stratum corneum from the adhesive surface.

Hydrophilic Components:

The hydrophilic component is present in a dispersed state in the hydrophobic component. The hydrophilic component is preferably a component that contributes to allowing the stratum corneum adhering to the adhesive composition to be peeled from the hydrophobic component. Further, the hydrophilic component is also preferably a component that enables the adhesive composition to satisfy the later-described range regarding water absorption rate, because the later-described water absorption rate is dependent on the hydrophilic component.

"Hydrophilic" as referred to herein not only encompasses "water-soluble", which means that a component is soluble in water, but may also encompass properties having high affinity to water although being water-insoluble. For example, hydrophilic components may encompass components that gel by taking in water, and components exhibiting water-absorbent action.

For the hydrophilic component, it is possible to use a hydrophilic polymer; for example, a compound used as a water-soluble thickener may be used. For example, the hydrophilic component may contain at least one selected from sugars, polysaccharides, and derivatives thereof.

For example, the hydrophilic component may preferably be at least one selected from water-soluble carboxymethyl cellulose (CMC) and salts thereof (e.g., water-soluble sodium CMC), water-insoluble carboxymethyl cellulose (CMC) and salts thereof (e.g., water-insoluble sodium CMC), alginic acid and salts thereof (e.g., sodium alginate, calcium alginate), vinyl acetate/vinylpyrrolidone copolymer (PVP-VA), polyvinylpyrrolidone, polyvinylpolypyrrolidone, and partially saponified vinyl acetate. Particularly, from the viewpoint of accuracy in biological substance measurement, the hydrophilic component is preferably a non-ionizing component such as PVP-VA copolymer.

Water-insoluble CMC is hydrophilic, within the meaning described above. The water-insoluble CMC may be, for example, an alkali metal salt of carboxymethyl cellulose. Water-soluble CMC and water-insoluble CMC can be distinguished from one another by the degree of etherification (degree of carboxymethylation). The degree of etherification is preferably 0.5 mol/C6 or less, more preferably 0.4 mol/C6 or less, even more preferably 0.3 mol/C6 or less. The degree of etherification is preferably 0.1 mol/C6 or greater, more preferably 0.2 mol/C6 or greater. Setting the degree of etherification within this range can reduce the water absorbency of the adhesive composition, and can thereby increase the amount of biological substance extracted from the collected stratum corneum. An example of a usable commercial product of water-insoluble CMC includes Sunrose (registered trademark) SLD (from Nippon Paper Industries Co., Ltd.).

The degree of etherification, as referred to herein, is the average number of carboxymethyl groups per anhydroglucose unit. The degree of etherification of the carboxymethyl cellulose compound can be measured, for example, by the naphthalene diol method. In the naphthalene diol method, concentrated sulfuric acid is added to carboxymethyl cellulose compound which is then heated, to produce glycolic acid by decomposition. The glycolic acid is subjected to reaction with 2,7-dihydroxynaphthalene, causing it to give a purplish red to reddish color. The degree of etherification can be found by measuring the absorbance of the solution at 530 nm.

The amount of the hydrophilic component may be smaller than the hydrophobic component. The content by percentage of the hydrophilic component is preferably 10% by mass or greater relative to the mass of the adhesive composition. The content by percentage of the hydrophilic component may be 15% by mass or greater, 20% by mass or greater, or 25% by mass or greater, relative to the mass of the adhesive composition. If the content by percentage of the hydrophilic component is less than 10% by mass, it may not be possible to sufficiently extract biological substances from the collected stratum corneum into the extraction solvent. The content by percentage of the hydrophilic component is preferably 55% by mass or less, more preferably 50% by mass or less, even more preferably 45% by mass or less, further more preferably 40% by mass or less, relative to the mass of the adhesive composition. If the content by percentage of the hydrophilic component exceeds 55% by mass, adhesive force may deteriorate, which may make it impossible to collect a sufficient amount of stratum corneum. Also, accurate measurement of biological substances may be hindered, due to an increase in the amount of absorption of the biological substance-containing extraction solvent and/or an increase in the amount of elution of the hydrophilic component.

Other Components:

The adhesive composition may further contain other additives in amounts that do not inhibit the effects of the present disclosure. Examples of additives may include surfactants, antioxidants, fillers, antiseptics, and perfumes.

Examples of surfactants may include nonionic surfactants. The nonionic surfactants are preferably hydrophilic surfactants. Examples of usable nonionic surfactants may include propylene glycol fatty acid esters, glycerin fatty acid esters, and polyglycerol fatty acid esters. An example of a propylene glycol fatty acid ester may include propylene glycol monocaprylate. An example of a glycerin fatty acid ester may include polyoxyethylene glyceryl isostearate. The average number of moles of oxyethylene units in a polyoxyethylene chain may be, for example, 10 to 100. The presence of a surfactant in the adhesive composition is thought to enable improvement in the efficiency of extracting biological substances.

Examples of antioxidants may include dibutylhydroxytoluene (BHT), dibutylhydroxyanisole (BHA), sodium bisulfate, sodium sulfite, ascorbic acid, and ascorbic acid esters.

Examples of fillers may include silica, silicates (e.g., aluminum silicate, magnesium silicate), calcium carbonate, magnesium carbonate, barium sulfate, calcium sulfate, calcium sulfite, zinc oxide, and titanium dioxide.

Examples of antiseptics may include ethyl p-hydroxybenzoate, propyl p-hydroxybenzoate, and butyl p-hydroxybenzoate.

The content by percentage of additive(s) in the adhesive composition is preferably 5% by mass or less, more preferably 3% by mass or less, even more preferably 2% by mass or less, further more preferably 1% by mass or less, relative to the mass of the adhesive composition. Adhesive properties may be affected if the content by percentage of other components exceeds 5% by mass. For example, the content by percentage of nonionic surfactant(s) may be 0.5% by mass or greater, or 1% by mass or greater; the content by percentage of nonionic surfactant(s) may be 5% by mass or less, or 3% by mass or less.

Adhesiveness:

The adhesive force (tack force) of the adhesive composition is preferably 3 N/20 mm or greater, more preferably 4 N/20 mm or greater. If the adhesive force is less than 3 N/20 mm, a sufficient amount of stratum corneum cannot be attached. The adhesive force of the adhesive composition is preferably 12 N/20 mm or less, more preferably 10 N/20 mm or less, even more preferably 9 N/20 mm or less. If the adhesive force exceeds 12 N/20 mm, a subject's skin may get damaged. Adhesive force can be measured in conformity to JIS Z0237.

Water Absorption Rate:

The water absorption rate of the hydrophilic component is preferably 250% or less, more preferably 200% or less, even more preferably 150% or less, further more preferably 100% or less, further more preferably 70% or less, further more preferably 50% or less, further more preferably 20% or less, further more preferably 10% or less. If the water absorption rate exceeds 250%, the adhesive composition may absorb a large amount of extraction solvent, which may lead to inaccurate measurement of the amount of collected biological substance.

The water absorption rate of the adhesive composition can be measured according to the following method. First, a 25×25×0.125 mm rectangular parallelepiped measurement sample is cut out from the adhesive composition. Herein, a measurement sample before being subjected to immersion is called "initial sample". The mass of the initial sample is measured, and this is defined as "initial mass". Next, the initial sample is immersed in ion-exchanged water for 24 hours. A sample immersed for 24 hours is called "immersed sample". Then, the mass of the immersed sample is measured, and this is defined as "post-immersion mass". The water absorption rate can be calculated from the following equation (1) by employing the initial mass and the post-immersion mass.

Water absorption rate (%)=(Post-immersion mass−Initial mass)/Initial mass×100.    (1):

The adhesive composition may have a strength that does not undergo rupture when subjected to tensile stress at the time of, for example, collecting the stratum corneum from the skin or preparing a stratum corneum-collecting instrument as described further below.

The adhesive composition according to the first embodiment is used for collecting the stratum corneum from a subject's skin and for extracting a biological substance from the collected skin. A method for using the adhesive composition will be described further below in the third embodiment.

For example, the adhesive composition according to the first embodiment can be used for extracting, from the stratum corneum, skin-related factors as biological substances. Examples of biological substances that can be extracted from the stratum corneum adhering to the adhesive composition may include at least one selected from squamous cell carcinoma antigens (e.g., SCCA1), superoxide dismutases (SODs; e.g., SOD1, SOD2), interleukin-1 (e.g., IL-1ra, IL-1α, IL-1β), matrix metalloproteinases (e.g., MMP9, MMP2), glycoproteins (e.g., AZGP1), cathepsins (e.g., cathepsin A, cathepsin B, cathepsin S), S100 proteins (e.g., S100A7, S100A8, S100A9), and vascular endothelial growth factors (e.g., VEGF).

Examples of other biological substances that can be extracted from the stratum corneum adhering to the adhesive composition may include at least one selected from kallikrein-related peptidases (KLKs; e.g., KLK-5, KLK-7, KLK-8, KLK-11, KLK-12, KLK-13), elafin (elastase-specific inhibitor/skin-derived antileukoprotease), tumor necrosis factor-alpha (TNF-α) converting enzyme (TACE), and calmodulin-like 5 (CALML-5).

The biological substance(s) contained in the stratum corneum adhering to the adhesive composition can be extracted into a solvent according to a simple process of bringing the stratum corneum, which is adhering to the adhesive composition, into contact with the extraction solution, without requiring troublesome tasks such as ultrasonic treatment and/or centrifugal separation. Even if the solvent is to be shaken, a shaking device can be used, and no other troublesome task is required. Further, immersion of the adhesive composition will only take a few minutes. Thus, the time required from collecting the stratum corneum to extraction of biological substances can be reduced significantly. Further, large-scale devices, such as a centrifugal separator, are not necessary. Thus, skin check/examination etc. can be done quickly and easily in medical settings, pharmacies, cosmetics stores, etc., based on extracted biological substances, without placing temporal burden to a subject.

The adhesive composition of the present disclosure has a moderate tack force suitable for collecting the stratum corneum. More specifically, with this adhesive composition, it is possible to collect a sufficient amount of stratum corneum per unit area of the adhesive composition, while suppressing infliction of strong pain to a subject when peeling the adhesive composition off from the skin and also suppressing occurrence of skin disorder in a subject.

With the adhesive composition of the present disclosure, the area of attachment of the adhesive composition per measurement can be reduced. This can further reduce the burden on a subject's skin. This also enables pinpoint measurement of the amount of presence of biological substances. For example, even in a case where the stratum corneum is collected from the face, it is possible to compare, for example, biological substances in a region at the inner corner of the subject's eye and in a region at the tail of the subject's eye.

The adhesive composition has moderate softness, extensibility, and elasticity. Thus, the adhesive composition can easily deform so as to conform to the shape/contour of a subject's skin, and can also be easily attached and removed without undergoing rupture etc.

It is also possible to efficiently extract a biological substance from the stratum corneum adhering to the adhesive composition. Thus, a biological substance-containing solution having a higher concentration can be prepared from a smaller amount of stratum corneum. If, for example, a sufficient amount of biological substance cannot be extracted from a given amount of stratum corneum adhering to the adhesive, it will be difficult to measure the biological substance contained in the extraction solution. Otherwise, a larger amount of stratum corneum will need to be collected, which will be a burden on a subject and will also increase the workload for collecting the biological substance.

A method for producing the adhesive composition of the present disclosure will be described. The adhesive composition of the present disclosure can be prepared by, for example, employing known methods for producing adhesive skin patches, without limitation to a specific method. For example, in cases where a thermoplastic polymer is contained as a hydrophobic component, a mixture of hydrophobic components can be kneaded while being heated until the mixture becomes uniform, and then hydrophilic components (and additives) can be added gradually thereto and be kneaded until uniform, to produce an adhesive composition. The adhesive composition can then be given into a desired shape (e.g., a sheet shape) by using, for example, a hot extruder. Alternatively, a mixed solution can be formed by mixing a solution of hydrophobic components and a solution of hydrophilic components, and then the mixed solution can be dried in a desired shape (e.g., a sheet shape), to produce an adhesive composition.

Next, a stratum corneum-collecting instrument according to a second embodiment of the present disclosure will be described. The stratum corneum-collecting instrument of the present disclosure is an instrument for collecting the stratum corneum from the skin (human skin).

A stratum corneum-collecting instrument 10 according to a first mode will be described. FIG. 1 is a schematic plan view of a stratum corneum-collecting instrument according to the first mode. FIG. 2 is a schematic cross-sectional view of the stratum corneum-collecting instrument taken along line II-II in FIG. 1.

The stratum corneum-collecting instrument 10 includes: an adhesive composition 1 according to the first embodiment; and a support 2 that has the adhesive composition 1 provided to at least a portion thereof and supports the adhesive composition 1. In the mode illustrated in FIGS. 1 and 2, the adhesive composition 1 is provided on one surface of the support 2. The shape of the adhesive composition 1 and the support 2 is not particularly limited. The adhesive composition 1 and the support 2 may be, for example, circular, elliptic, polygonal, or amorphous. The stratum corneum-collecting instrument 10 may be cuttable/separable into a desired size.

The support 2 is for facilitating attachment/removal of the adhesive composition 1 to/from a subject's skin. Preferably, the support 2 has flexibility so as to enable deformation along the skin. Also, preferably, the support 2 has a strength that does not undergo rupture when the stratum corneum-collecting instrument 10 is attached/removed to/from the skin. The tensile strength of the support 2 is preferably 8 N/20 mm or greater. Also, preferably, the support 2 does not have extensibility. The support 2 may assume any shape, such as sheet-shaped, rod-shaped, or other three-dimensional shapes, depending on the form of the stratum corneum-collecting instrument 10. For the support 2, it is possible to use, for example, paper or a resin film made of, e.g., a polyester such as polyethylene terephthalate, polyethylene, polypropylene, or polycarbonate. In cases where the support 2 is sheet-shaped, the thickness of the support 2 can be set as appropriate depending on handleability, usage, etc. The thickness of the support 2 may be, for example, 4 µm or greater, 10 µm or greater, or 20 µm or greater. Also, the thickness of the support 2 may be, for example, 100 µm or less, or 50 µm or less.

The stratum corneum-collecting instrument 10 may further include a protection sheet (not illustrated) for protecting the adhesive composition 1's surface for collecting the stratum corneum.

The adhesive composition 1 preferably has a flat-plate shape along the support 2. To allow collection of a sufficient amount of stratum corneum, the area of the adhesive composition 1 in a section that comes into contact with a subject's skin is preferably 2 $cm^2$ or greater, more preferably 4 $cm^2$ or greater. To enable the adhesive composition to come into contact with the sulcus cutis and/or crista cutis, the thickness of the adhesive composition 1 is preferably 0.05 mm or greater, more preferably 0.08 mm or greater. Further, to suppress the intake of biological substance due to absorption of the extraction solvent, the thickness of the adhesive composition 1 is preferably 0.5 mm or less, more preferably 0.3 mm or less.

The adhesive composition 1 and the support 2 may be joined by the adhesive force of the adhesive composition 1. Alternatively, to prevent peeling during use, the adhesive composition 1 and the support 2 may be joined by an adhesive (not illustrated) having a higher adhesive force than the adhesive composition 1. For the adhesive, it is preferred to use an adhesive having low water absorbency so as not to absorb biological substances during extraction.

As in the stratum corneum-collecting instrument 20 illustrated in FIG. 3, the adhesive composition 1 may be provided on both surfaces of the support 2. According to this stratum corneum-collecting instrument 20, a greater amount of biological substance can be acquired with a single extraction process.

A stratum corneum-collecting instrument 30 according to a second mode will be described. FIG. 4 is a schematic perspective view of a stratum corneum-collecting instrument according to the second mode. FIG. 5 is a schematic perspective view of a support illustrated in FIG. 4.

The stratum corneum-collecting instrument 30 illustrated in FIG. 4 includes: an adhesive composition 1 according to the first embodiment; and a support 12 that has the adhesive composition 1 provided to at least a portion thereof and supports the adhesive composition 1. As illustrated in FIG. 5, the support 12 includes: a grip portion 12a to be held by a user (tester) to handle the stratum corneum-collecting instrument 30; and a stratum corneum-collecting portion 12b, the adhesive composition 1 being provided to at least a portion thereof. The grip portion 12a may assume any shape, so long as it is a shape that enables a user to handle the stratum corneum-collecting instrument 30. The grip portion 12a may be shaped so as to conform to the shape of a container as described in the third embodiment further below. The stratum corneum-collecting portion 12b may be integral with the grip portion 12a. The stratum corneum-collecting portion 12b may extend from the grip portion 12a. To facilitate collection of stratum corneum from a subject, the stratum corneum-collecting portion 12b may assume a shape capable of providing a suitable distance between the grip portion 12a and the adhesive composition 1, such as columnar, rod-shaped, tubular, or plate-shaped.

In order to facilitate the task of collecting the stratum corneum, the adhesive composition 1 is preferably provided to the tip-end side of the stratum corneum-collecting portion 12b opposite from the side of the grip portion 12a. In cases where the stratum corneum-collecting portion 12b has a flat-plate shape, the adhesive composition 1 may be provided to only one surface of the stratum corneum-collecting portion 12b, or may be provided to both surfaces. FIG. 4 illustrates a mode wherein the adhesive composition 1 is provided only to the tip-end portion of the stratum corneum-collecting portion 12b, but the adhesive composition 1 may be provided to any section of the stratum corneum-collecting portion 12b. The stratum corneum-collecting instrument 30 may be configured such that the adhesive composition 1 can be replaced to make the support 12 reusable.

With the stratum corneum-collecting instrument 30 of the second mode, a user can easily collect the stratum corneum from a subject. Also, the biological substance can be extracted easily from the collected stratum corneum.

Each of the stratum corneum-collecting instruments 10, 20, 30 according to the second embodiment can be manufactured by attaching a shaped adhesive composition 1 onto a support 2, 12. Alternatively, each stratum corneum-collecting instrument 10, 20, 30 can be manufactured by applying, onto a support 2, 12, a solution obtained by dissolving an adhesive composition 1 in a solvent, and drying the same.

With the stratum corneum-collecting instrument according to the second embodiment, stratum corneum can be collected easily from a subject.

Next, a biological substance extraction kit according to a third embodiment of the present disclosure will be described. FIG. 6 is a schematic perspective view of an example of a biological substance extraction kit. Hereinbelow, a biological substance extraction kit 40 including a stratum corneum-collecting instrument 30 according to the second embodiment illustrated in FIG. 4 will be described as an example of a biological substance extraction kit of the third embodiment. FIG. 7 illustrates a schematic perspective view of a biological substance extraction kit having a different form from that illustrated in FIG. 6.

The biological substance extraction kit 40 includes: a stratum corneum-collecting instrument 30 according to the second embodiment; and a container 41. The biological substance extraction kit 40 may further include, in the container 41, an extraction solvent (not illustrated) for extracting a biological substance from the stratum corneum. The extraction solvent may be introduced into the container upon use.

The container 41 may have a bottomed cylindrical shape. The container 41 can receive the adhesive composition 1 through an opening 41a. In a state where the adhesive composition 1 is housed, it is preferred that the adhesive composition 1 does not contact the inner surface of the container 41, to allow the surface of the adhesive composition 1 to contact the extraction solvent. The container 41 and/or the support 12 may preferably include a positioning portion (not illustrated) that allows the position of the adhesive composition 1 to be fixed with respect to the inner surface of the container 41 by establishing engagement between a portion of the grip portion 12a and a portion of the container 41.

It is preferred to shape the container 41 such that, in a state where the adhesive composition 1 is housed in the container 41 and/or a state where the stratum corneum-collecting instrument 30 is attached to the container 41, a gap is present between the adhesive composition and the inner surface of the container, so that the amount of extraction solvent required for extracting a biological substance can be made small.

It is also preferable to configure the kit such that, in a state where the adhesive composition 1 is housed in the container 41 and/or a state where the stratum corneum-collecting instrument 30 is attached to the container 41, the extraction solvent inside the container 41 does not leak out. For example, the container 41 and/or the support 12 may further include a leakage-preventing portion (not illustrated), such as a gasket. Alternatively, the container and the support may be provided with a thread ridge (or thread groove) so that the container 41 and the support 12 can be screwed together. Also, for example, the grip portion 12a of the support 12 may also serve as a lid. Alternatively, as illustrated in FIG. 7, a biological substance extraction kit 43 may further include a lid 44 that can be detachably attached to the opening 41a of the container 41 in a state where the stratum corneum-collecting instrument 30 is attached to the container 41 and the adhesive composition 1 is housed therein.

At least one of the container 41, the support 12 and the lid 43 may also have an outlet (not illustrated) from which liquid inside the container 41 can be discharged in a state where the support 12 is attached to the container 41 and/or a state where the adhesive composition 1 is housed in the container 41.

Other than the stratum corneum-collecting instruments and biological substance extraction kits illustrated in FIGS. 1 to 7, configurations wherein the adhesive composition of the present disclosure is employed for the adhesive layer of the stratum corneum-collecting instrument and stratum corneum collecting/detecting kit disclosed in Patent Literature 1 may be considered to be within the scope of the stratum corneum-collecting instrument and the biological substance extraction kit according to the present disclosure. Matters disclosed in Patent Literature 1 are incorporation herein by reference, and thus detailed description of the stratum corneum-collecting instrument and stratum corneum collecting/detecting kit of Patent Literature 1 is omitted herein.

With the biological substance extraction kit of the present disclosure, a biological substance can be extracted easily from the stratum corneum adhering to the adhesive composition.

Next, a biological substance collection method according to a fourth embodiment of the present disclosure will be described. FIG. 8 is a flowchart for describing a biological substance collection method according to the fourth embodiment. FIG. 9 is a conceptual diagram for illustrating a principle behind the biological substance collection method.

Note, however, that FIG. 9 merely illustrates a conjectural theory, and the biological substance collection method of the present disclosure should not be construed as being limited to the theory illustrated in FIG. 9.

First, an adhesive composition 1 according to the first embodiment is attached to the skin of a subject (S1). Preferably, the adhesive composition 1 is placed in tight contact with the skin. The contact area between the adhesive composition 1 and the skin is preferably 2 cm$^2$ or greater, more preferably 4 cm$^2$ or greater. It will suffice if the length of time for attaching the adhesive composition is at least 5 seconds. Then, the adhesive composition 1 is removed from the subject's skin, to cause the subject's stratum corneum 51 to adhere to the adhesive composition 1 (S2; FIG. 9(a)).

Next, at least a portion of the adhesive composition 1, to which the stratum corneum 51 has adhered, is brought into contact with an extraction solvent 61 (S3; FIG. 9(b)). The entire adhesive composition 1 may be immersed in the extraction solvent 61. It is preferred that the extraction solvent 61 has affinity for the hydrophilic component 1a, and is preferably an aqueous solution. The length of time of contact between the adhesive composition 1 and the extraction solvent 61 is preferably 1 minute or longer, more preferably 5 minutes or longer. In step S3, to facilitate extraction of a biological substance 52 contained in the stratum corneum 51, the solvent 61, or the container containing the solvent 61, may be shaken while keeping the adhesive composition 1 and the extraction solvent 61 in contact with one another. Alternatively, the solvent may be subjected to ultrasonic waves while keeping the adhesive composition 1 and the extraction solvent 61 in contact with one another. The temperature of the solvent 61 is preferably from 20° C. to 40° C. The pH of the solvent 61 is preferably from 6 to 9.

At this time, the hydrophilic component 1a in the adhesive composition 1 interacts in an affinitive manner with the solvent 61. For example, the hydrophilic component 1a may elute into the solvent 61, or may take in the solvent 61 and swell. This reduces the tack force of the hydrophobic component 1b in the solvent 61, and thereby allows the solvent 61 to easily enter between the adhesive composition 1 and the stratum corneum 51. This is considered to be the reason why the biological substance 52 in the stratum corneum 51 can easily elute into the solvent 61 (FIG. 9(c)). In FIG. 9(c), the hydrophilic component 1a is illustrated as if it dissolves into the solvent 61, but the hydrophilic component 1a may be insoluble in the solvent 61.

For the extraction solvent, it is possible to use, for example, a buffer used for life-science research. The extraction solvent may be, for example, a solution containing a buffer and a nonionic surfactant. For the extraction solvent, it is possible to use, for example, a phosphate buffer or Tris-HCl buffer containing tris(hydroxymethyl)aminomethane. An example of a usable nonionic surfactant may include polyoxyethylene sorbitan monolaurate (Tween (registered trademark) 20). The concentration of the nonionic surfactant in the extraction solvent may be from 0.01 to 5% by mass. The extraction solvent may contain sodium chloride to produce a physiological saline.

With the biological substance collection method of the present disclosure, a biological substance can be collected from the stratum corneum easily and in a short time. For example, the biological substance collection method of the present disclosure can do away with such tasks as cutting up the adhesive composition, inserting the adhesive composition into a tube, applying ultrasonic vibration to the tube, and centrifugal separation. Even if the solvent requires shaking, this can be achieved simply by setting the solvent to a shaking device, which is not that troublesome.

EXAMPLES

The adhesive composition of the present disclosure will be described below according to examples. Note, however, that the adhesive composition of the present disclosure is not limited to the following examples. The unit employed for indicating the contents by percentage shown in the Tables is percent by mass (mass %).

Test Examples that are compiled in a single table provide data acquired from stratum corneum collected from the same subject on the same day. The amount of biological substance and protein obtained from the stratum corneum differs subject by subject, and also differs day by day even if collected from the same subject. Thus, even if two adhesive compositions have the same makeup, they are described as different Test Examples if the subject or the stratum corneum sampling date is different.

Test Examples 1 and 2

In Test Example 1, an adhesive composition according to the first embodiment having the makeup shown in Table 1 was prepared, and the protein extraction amount was measured. In Test Example 1, vinyl acetate/vinylpyrrolidone copolymer (PVP-VA) was used as a hydrophilic component. Among the hydrophobic components, component (1) acts as a tackifier. Components (2) and (3) act as shape retention agents. The viscosity molecular weight of component (3) was 55,000. Component (4) acts as a softener. In Test Example 2, a cellophane tape, conventionally used as a stratum corneum-collecting tape, was used to collect the stratum corneum, and the protein extraction amount was measured as in Test Example 1. The measurement results are shown in Table 2. The results in Table 2 show an average value of measurements performed twice for each example.

In Test Example 1, the adhesive composition of Test Example 1 having an area of 6.25 cm$^2$ (thickness: 0.1 cm) was attached to the thigh for 60 seconds, to make stratum corneum adhere to the adhesive composition. A phosphate buffer containing 0.1% by mass of polyoxyethylene (20) sorbitan monolaurate (Tween (registered trademark) 20) was used as an extraction solvent. Then, while keeping the adhesive composition in contact with the extraction solvent contained in a container, the container was shaken. After 30 minutes from shaking, the extraction solvent was collected. The amount of SCCA1 was measured using enzyme-linked immunosorbent assay (ELISA) method. Note that extraction of SCCA1 was also possible by leaving the adhesive composition standing in the extraction solvent for 5 minutes.

In Test Example 2, a cellophane tape having an area of 6.25 cm$^2$ was attached to the thigh for 60 seconds, to make stratum corneum adhere to the adhesive surface of the cellophane tape. Next, the cellophane tape was cut up, and each piece of cut-up tape was immersed in an extraction solvent contained in a centrifuge tube. The extraction liquid containing the tape was subjected to ultrasonic treatment with an ultrasonic homogenizer, and was then subjected to centrifugal separation. The extraction liquid was collected from each of the tubes, and the amount of SCCA1 was measured as in Test Example 1.

The time required from sampling of the stratum corneum to collection of the extraction solution using 10 samples each of the adhesive composition and the cellophane tape was compared between Test Examples 1 and 2. The required time for Test Example 1 was about 20 to 45 minutes (varied depending on extraction time), whereas for Test Example 2, the required time was 150 minutes, which was over three times that for Test Example 1. This shows that the adhesive composition of the present disclosure can significantly simplify the tasks required for extraction and can also significantly reduce the time required for extraction.

Test Example 2 requires such devices as a centrifugal separator and an ultrasonic treatment device for the extraction task. In contrast, Test Example 1 requires no such device for the extraction task. Thus, skin check can be performed even in a small space such as a store counter.

When comparing the biological substance extraction amount, the results show that the adhesive composition of Test Example 1 was able to collect three times the amount of biological substance compared to the cellophane tape of Test Example 2. Thus, this shows that the adhesive composition of the present disclosure can collect a biological substance in the stratum corneum more efficiently than the cellophane tape.

Further, the subject revealed that the adhesive composition of the present disclosure caused less irritation to the skin at the time of peeling from the skin, compared to the cellophane tape.

TABLE 1

| | | | Test Example 1 |
|---|---|---|---|
| (1) | Hydrophobic | Rosin ester *1 | 36 |
| (2) | components | SIS block copolymer *2 | 17 |
| (3) | | Polyisobutylene | 10 |
| (4) | | Liquid paraffin | 7 |
| (5) | Hydrophilic component | PVP-VA copolymer | 30 |
| | | Total | 100 |
| | | Water absorption rate (%) | 5 |

*1: Pine Crystal (registered trademark) KE-311 (Arakawa Chemical Industries, Ltd.)
*2: DX401JS (Kraton Corporation)

TABLE 2

| | | SCCA1 extraction amount (ng/ml) | Time required for processing 10 samples (minutes) |
|---|---|---|---|
| Test Example 1 | Composition according to Table 1 | 3.18 | about 20-45 |
| Test Example 2 | Cellophane tape *3 | 1.06 | about 150 |

*3: Cellotape (registered trademark) (Nichiban Co., Ltd.)

Test Examples 3 to 6

Test Examples 3 to 6 compared the adhesive composition of the present disclosure and various commercially available corneum checkers. The adhesive composition of Test Example 3 was identical to the adhesive composition shown in Table 1; stratum corneum collection and protein extraction were performed as in Test Example 1, and the total mass of extracted protein was measured. The corneum checker of Test Example 4 uses a medical-use acrylic adhesive. The corneum checker of Test Example 5 uses an acrylic copolymer. As for the corneum checkers of Test Examples 4 to 6, the stratum corneum was collected according to the instructions for use of each corneum checker, and protein was extracted according to the same conditions as in Test Example 3, to measure the total amount of protein extracted from the stratum corneum. The total protein amount was measured using the Lowry method. The amount of extraction solvent was determined depending on the area for collecting the stratum corneum (i.e., the area of the adhesive). The measurement results are shown in Table 3. The results in Table 3 show the protein extraction amount per 1 $cm^2$ of the respective adhesive, and the shown amount is an average value of measurements performed twice for each adhesive.

The results show that the adhesive composition of Test Example 1 was able to collect around 1.3 to 5.8 times the amount of protein per unit area compared to the stratum corneum collecting tapes of Test Examples 4 to 6. This shows that the adhesive composition of the present disclosure can collect a biological substance in the stratum corneum more efficiently than commercially available stratum corneum-collecting products.

TABLE 3

| | | Total protein extraction amount ($\mu g/(ml \cdot cm^2)$) |
|---|---|---|
| Test Example 3 | Composition according to Table 1 | 2.67 |
| Test Example 4 | Stratum corneum tape *4 | 0.46 |
| Test Example 5 | D-SQUAME tape *5 | 2.00 |
| Test Example 6 | Corneum checker *6 | 0.89 |

*4: Taiki Corporation
*5: Promotool Corporation
*6: Asahi Biomed

Test Examples 7 to 9

Adhesive compositions having the respective makeup shown in Table 4 were prepared, and the respective biological substance extraction amounts were compared. In Test Example 7, water-insoluble sodium carboxymethyl cellulose (water-insoluble CMC) was used as a hydrophilic component. In Test Examples 8 and 9, water-soluble sodium carboxymethyl cellulose (water-soluble CMC) was used. Further, in Test Examples 7 to 9, an alicyclic saturated hydrocarbon resin was used in addition to rosin ester as a tackifier, and also, the blending proportions of the respective hydrophobic components were changed. In Test Examples 7 to 9, a Tris buffer containing 0.1% by mass of polyoxyethylene (20) sorbitan monolaurate (Tween (registered trademark) 20) was used as the extraction solvent. Each adhesive composition was immersed in the extraction solvent and left standing for 30 minutes. Otherwise, the stratum corneum was collected as in Test Example 1, and the amount of SCCA1 was measured. The measurement results are shown in Table 4.

Test Example 7 was able to extract a sufficient amount of biological substance. In Test Examples 8 and 9, the biological substance extraction amount was smaller but within a permissible range. This suggests that, at least according to the compositions of Test Examples 7 to 9, a biological substance can be extracted easily and efficiently. It was also found that, for example, at least one of a rosin ester or an alicyclic saturated hydrocarbon resin can be used as a tackifier. It was also found that, for example, at least one of SIS block copolymer or polyisobutylene can be used as a shape retention agent. It was also found that, for example, liquid paraffin can be used as a softener.

It was also found that at least one of water-insoluble CMC or water-soluble CMC can be used as a hydrophilic component, but Test Example 7, which used water-insoluble CMC, was able to collect 4 to 5 times the amount of biological substance compared to Test Examples 8 and 9, which used water-soluble CMC. The reason why the extraction amount dropped in Test Examples 8 and 9 is considered to be because the use of water-soluble CMC increased the water absorbency of the adhesive composition. More specifically, it is considered that, in Test Examples 8 and 9, the biological substance-containing solution was absorbed by the adhesive composition, which resulted in a reduction in the extraction amount.

TABLE 4

|  |  | Test Example | | |
|---|---|---|---|---|
|  |  | 7 | 8 | 9 |
| (1) Hydrophobic | Rosin ester *1 | — | 5.6 | 1.4 |
| (2) components | Alicyclic saturated hydrocarbon resin *7 | 28.0 | 22.4 | 12.6 |
| (3) |  | SIS block copolymer *2 | 17.5 | 17.5 | 21.0 |
| (4) |  | Polyisobutylene | 17.5 | 17.5 | 12.6 |
| (5) |  | Liquid paraffin | 7.0 | 7.0 | 14.0 |
| (6) Hydrophilic | Water-insoluble CMC | 30.0 | — | — |
| (7) component | Water-soluble CMC | — | 30.0 | 30.0 |
|  | Total | 100 | 100 | 100 |
| SCCA1 extraction amount (ng/ml)/14.4 cm$^2$ |  | 4.50 | 0.86 | 0.82 |

*7: Arkon (registered trademark) from Arakawa Chemical Industries, Ltd.

Test Examples 10 and 11

In Test Examples 10 and 11, the type of tackifier was varied while using the same hydrophilic component and keeping the content by percentage thereof the same, and the biological substance extraction amount was measured. The stratum corneum collection method and the biological substance extraction method were the same as in Test Examples 7 to 9. The compositions and measurement results are shown in Table 5. The results in Table 5 show an average value of measurements performed three times for each example.

The results show that, regardless of whether the tackifier was a rosin ester or an alicyclic saturated hydrocarbon resin, it was possible to extract a sufficient amount of biological substance in the same manner as in Test Examples 7 to 9. When comparing Test Example 10 and Test Example 11, Test Example 10 was able to extract more biological substance than Test Example 11. This suggests that rosin esters are more preferable as a tackifier than alicyclic saturated hydrocarbon resins.

TABLE 5

|  |  |  | Test Example | |
|---|---|---|---|---|
|  |  |  | 10 | 11 |
| (1) | Hydrophobic | Rosin ester *1 | 27.0 | — |
| (2) | components | Alicyclic saturated hydrocarbon resin *7 | — | 24.0 |
| (3) |  | SIS block copolymer *2 | 10.8 | 15.0 |
| (4) |  | Polyisobutylene | 16.2 | 15.0 |
| (5) |  | Liquid paraffin | 6.0 | 6.0 |
| (6) | Hydrophilic component | Water-insoluble CMC | 40.0 | 40.0 |
|  |  | Total | 100 | 100 |
|  |  | Water absorption rate (%) | 190 | 180 |
| SCCA1 extraction amount (ng/ml) (ng/ml)/7.5 cm$^2$ |  |  | 2.41 | 1.12 |

Test Examples 12 to 18

In Test Examples 12 to 18, adhesive compositions were prepared, wherein the tackifier and the shape retention agent in the hydrophobic components were blended in different proportions, and the respective biological substance extraction amounts were compared. The stratum corneum collection method and the biological substance extraction method were the same as in Test Examples 7 to 9. The compositions and measurement results are shown in Tables 6 to 8. The results in Tables 6 to 8 show an average value of measurements performed twice for each example. The makeup of Test Example 17 is the same as in Test Example 1. Test Examples 13, 15, and 16 have the same makeup. The makeup of Test Example 12 is the same as in Test Example 23 described further below.

In Test Examples 12 and 13, the SCCA1 extraction amount was insufficient, so the total protein extraction amount was measured. Note, however, that the reason why SCCA1 was not extracted is considered to be attributable to the state of the subject's skin, rather than being caused by the adhesive composition. Also in Test Example 16, the SCCA1 extraction amount was small; this is also considered to be attributable to the state of the subject's skin, rather than being caused by the adhesive composition. More specifically, when comparing Test Example 1 and Test Example 17, the biological substance extraction amount is smaller in Test Example 17, even though the makeup of the adhesive compositions is the same; thus, the small biological substance extraction amounts of the Test Examples shown in Table 8 are attributable to the state of the subject's skin. Similarly, considering that the makeup of Test Examples 13, 15, and 16 is the same, the small biological substance extraction amounts shown in Tables 6 and 7 are attributable to the state of the subject's skin.

In Test Examples 12 and 13, the respective blending proportions of the tackifier and the shape retention agent were changed, while keeping the blending proportion of the softener the same. In Test Examples 14 and 15, the respective blending proportions of the materials in the shape retention agent were changed, while keeping the respective blending proportions of the tackifier and the softener the same. As described above, these compositions had a low water absorption rate (less than 10%), and were capable of extracting a sufficient amount of biological substance.

In Test Examples 16 to 18, the blending proportion of the tackifier was changed. As described above, these compositions had a low water absorption rate, and were capable of extracting a sufficient amount of biological substance. This suggests that the compositions of Test Examples 12 to 18 can suitably be used as adhesive compositions.

TABLE 6

|  |  |  | Test Example | |
|---|---|---|---|---|
|  |  |  | 12 | 13 |
| (1) | Hydrophobic | Rosin ester *1 | 28.0 | 33.0 |
| (2) | components | SIS block copolymer *2 | 17.5 | 17.0 |
| (3) |  | Polyisobutylene | 17.5 | 13.0 |
| (4) |  | Liquid paraffin | 7.0 | 7.0 |
| (5) | Hydrophilic component | PVP-VA copolymer | 30.0 | 30.0 |
|  |  | Total | 100 | 100 |
|  |  | Water absorption rate (%) | 8 | 8 |
| Total protein extraction amount (μg/ml)/6.3 cm$^2$ |  |  | 14.7 | 16.2 |

TABLE 7

|   |   |   | Test Example 14 | Test Example 15 |
|---|---|---|---|---|
| (1) | Hydrophobic | Rosin ester *1 | 33.0 | 33.0 |
| (2) | components | SIS block copolymer *2 | 15.0 | 17.0 |
| (3) |   | Polyisobutylene | 15.0 | 13.0 |
| (4) |   | Liquid paraffin | 7.0 | 7.0 |
| (5) | Hydrophilic component | PVP-VA copolymer | 30.0 | 30.0 |
|   |   | Total | 100 | 100 |
|   |   | Water absorption rate (%) | 3 | 8 |
|   |   | SCCA1 extraction amount (ng/ml)/6.3 cm$^2$ | 1.19 | 1.04 |

TABLE 8

|   |   |   | Test Example 16 | Test Example 17 | Test Example 18 |
|---|---|---|---|---|---|
| (1) | Hydrophobic | Rosin ester *1 | 33.0 | 36.0 | 40.0 |
| (2) | components | SIS block copolymer *2 | 17.0 | 17.0 | 17.0 |
| (3) |   | Polyisobutylene | 13.0 | 10.0 | 16.0 |
| (4) |   | Liquid paraffin | 7.0 | 7.0 | 7.0 |
| (5) | Hydrophilic component | PVP-VA copolymer | 30.0 | 30.0 | 30.0 |
|   |   | Total | 100 | 100 | 100 |
|   |   | Water absorption rate (%) | 8 | 5 | 5 |
|   |   | SCCA1 extraction amount (ng/ml)/6.3 cm$^2$ | 0.76 | 1.06 | 1.34 |

Test Examples 19 to 21

Adhesive compositions were prepared by using water-insoluble CMC as a hydrophilic component and varying the content by percentage of the water-insoluble CMC, to compare the biological substance extraction amount. The stratum corneum collection method and the biological substance extraction method were the same as in Test Examples 7 to 9. The compositions and measurement results are shown in Table 9. The makeup of Test Example 20 is the same as in Test Example 10. The results in Table 9 show an average value of measurements performed three times for each example. FIG. 10 illustrates a graph showing a relationship between the content by percentage of the hydrophilic component, the water absorption rate and the SCCA1 extraction amount in Test Examples 19 to 21.

FIG. 10 shows that, with the increase in the content by percentage of the hydrophilic component, the water absorption rate increases proportionally, whereas the SCCA1 extraction amount decreases in inverse proportion. This suggests that, to increase the biological substance extraction amount, it is preferred that the adhesive composition has a lower water absorption rate. A suggested water absorption rate of the adhesive composition is preferably 250% or less, more preferably 200% or less, even more preferably 150% or less, further more preferably 100% or less, even more preferably 50% or less, further more preferably 10% or less. It is considered that, in Test Examples 19 to 21, the correlation between the water absorption rate and the biological substance extraction amount appeared more clearly than in the other Test Examples because the water absorption rate was higher than in the aforementioned Test Examples.

All of Test Examples 19 to 21 had a high biological substance extraction amount. This suggests that a biological substance can be extracted efficiently at least when the content of the hydrophilic component is from 25 to 55% by mass. The results also show a tendency that, as the content by percentage of the water-insoluble CMC decreases, the water absorption rate also decreases whereas the biological substance extraction amount increases. This suggests that the content by percentage of the hydrophilic component is preferably 50% by mass or less, more preferably 45% by mass or less, even more preferably 40% by mass or less. Note, however, that if the content by percentage of the hydrophilic component is too low, it is considered that the tack force becomes too strong as in the cellophane tape of Test Example 2, which may result in a reduction in the biological substance extraction amount.

Reference to the other Test Examples suggest that, in order to reduce the water absorption rate, it is preferred to use PVP-VA copolymer than water-insoluble CMC as the hydrophilic component.

TABLE 9

|   |   |   | Test Example 19 | Test Example 20 | Test Example 21 |
|---|---|---|---|---|---|
| (1) | Hydrophobic | Rosin ester *1 | 31.5 | 27.0 | 22.5 |
| (2) | components | SIS block copolymer *2 | 12.6 | 10.8 | 9.0 |
| (3) |   | Polyisobutylene | 18.9 | 16.2 | 13.5 |
| (4) |   | Liquid paraffin | 7.0 | 6.0 | 5.0 |
| (5) | Hydrophilic component | Water-insoluble CMC | 30.0 | 40.0 | 50.0 |
|   |   | Total | 100 | 100 | 100 |
|   |   | Water absorption rate (%) | 120 | 190 | 230 |
|   |   | SCCA1 extraction amount (ng/ml)/7.5 cm$^2$ | 2.62 | 2.41 | 2.26 |

Test Examples 22 to 24

Adhesive compositions were prepared by using PVP-VA copolymer as a hydrophilic component and varying the content by percentage of the PVP-VA copolymer, to compare the biological substance extraction amount. The stratum corneum collection method and the biological substance extraction method were the same as in Test Examples 7 to 9. The compositions and measurement results are shown in Table 10. The results in Table 10 show an average value of measurements performed twice for each example. The makeup of Test Example 23 is the same as in Test Example 12.

The adhesive compositions of Test Examples 22 to 24 all had a low water absorption rate and a sufficient biological substance extraction amount. This suggests that a biological substance can be extracted efficiently at least when the content of the hydrophilic component is 10% by mass or greater.

TABLE 10

|   |   |   | Test Example 22 | Test Example 23 | Test Example 24 |
|---|---|---|---|---|---|
| (1) |   | Rosin ester *1 | 34.0 | 28.0 | 22.0 |
| (2) | Hydrophobic | SIS block copolymer *2 | 21.3 | 17.5 | 13.8 |
| (3) | components | Polyisobutylene | 21.3 | 17.5 | 13.8 |
| (4) |   | Liquid paraffin | 8.5 | 7.0 | 5.5 |
| (5) | Hydrophilic component | PVP-VA copolymer | 15.0 | 30.0 | 45.0 |
|   |   | Total | 100 | 100 | 100 |
|   |   | Water absorption rate (%) | 8 | 2 | 7 |
|   |   | SCCA1 extraction amount (ng/ml)/6.3 cm$^2$ | 1.34 | 1.29 | 1.60 |

Test Examples 25 to 29

Test Examples 25 to 29 further included a nonionic surfactant in addition to the aforementioned components. The stratum corneum collection method and the biological substance extraction method were the same as in Test Examples 7 to 9, except that the extraction solvent was shaken during extraction. The compositions and measurement results are shown in Table 11. The results in Table 11 show an average value of measurements performed twice for each example.

All of Test Examples 25 to 29 had a low water absorption rate and a high biological substance extraction amount. This thereby suggests that, in order to increase the biological substance extraction amount, it is useful to add a nonionic surfactant, such as a propylene glycol fatty acid ester and/or a glycerin fatty acid ester. The content by percentage of the nonionic surfactant may be 0.5% by mass or greater. The content by percentage of the nonionic surfactant may be 5% by mass or less.

TABLE 11

|  |  | Test Example | 25 | 26 | 27 | 28 | 29 |
|---|---|---|---|---|---|---|---|
| (1) | Hydrophobic | Rosin ester *1 | 28.0 | 28.0 | 26.0 | 28.0 | 28.0 |
| (2) | components | SIS block copolymer *2 | 17.0 | 17.0 | 17.0 | 17.0 | 17.0 |
| (3) |  | Polyisobutylene | 17.0 | 17.0 | 17.0 | 17.0 | 17.0 |
| (4) |  | Liquid paraffin | 7.0 | 7.0 | 7.0 | 7.0 | 7.0 |
| (5) | Hydrophilic component | PVP-VA copolymer | 30.0 | 30.0 | 30.0 | 30.0 | 30.0 |
| (6) | Others | Propylene glycol monocaprylate *8 | 1.0 | — | — | — | — |
| (7) |  | PEG-20 glyceryl isostearate *9 | — | 1.0 | 3.0 | — | — |
| (8) |  | PEG-60 glyceryl isostearate *10 | — | — | — | 1.0 | — |
| (9) |  | PEG-90 glyceryl isostearate *11 | — | — | — | — | 1.0 |
|  |  | Total | 100 | 100 | 100 | 100 | 100 |
|  |  | Water absorption rate (%) | 4 | 14 | 6 | 9 | 5 |
|  |  | SCCA1 extraction amount (ng/ml)/6.3 cm$^2$ | 1.75 | 1.94 | 1.55 | 1.70 | 1.63 |

*8: NIKKOL (registered trademark) SEFSOL-218 (Nikko Chemicals Co., Ltd.)
*9: EMALEX (registered trademark) GWIS-120 (Nihon Emulsion Co., Ltd.)
*10: EMALEX (registered trademark) GWIS-160 (Nihon Emulsion Co., Ltd.)
*11: EMALEX (registered trademark) GWIS-190 (Nihon Emulsion Co., Ltd.)

The aforementioned Test Examples show that the content of the hydrophobic component may be 40% by mass or greater, 45% by mass or greater, 50% by mass or greater, 55% by mass or greater, or 60% by mass or greater, relative to the mass of the composition, and also show that the content of the hydrophobic component may be 95% by mass or less, 90% by mass or less, 85% by mass or less, 80% by mass or less, or 75% by mass or less, relative to the mass of the composition.

The aforementioned Test Examples show that the content of the tackifier may be 10% by mass or greater, 15% by mass or greater, 20% by mass or greater, or 25% by mass or greater, relative to the mass of the composition, and also show that the content of the tackifier may be 45% by mass or less, 40% by mass or less, or 35% by mass or less, relative to the mass of the composition.

The aforementioned Test Examples show that the content of the shape retention agent may be 15% by mass or greater, 20% by mass or greater, or 25% by mass or greater, relative to the mass of the composition, and also show that the content of the shape retention agent may be 50% by mass or less, 45% by mass or less, 40% by mass or less, or 35% by mass or less, relative to the mass of the composition.

The aforementioned Test Examples show that the content of the softener may be 3% by mass or greater, or 5% by mass or greater, relative to the mass of the composition, and also show that the content of the softener may be 20% by mass or less, 15% by mass or less, or 10% by mass or less, relative to the mass of the composition.

The aforementioned Test Examples show that the content of the hydrophilic component may be 5% by mass or greater, 10% by mass or greater, 15% by mass or greater, 20% by mass or greater, or 25% by mass or greater, relative to the mass of the composition, and also show that the content of the hydrophilic component may be 60% by mass or less, 55% by mass or less, 50% by mass or less, 45% by mass or less, or 40% by mass or less, relative to the mass of the composition.

The stratum corneum-collecting adhesive composition, the stratum corneum-collecting instrument, the biological substance extraction kit, and the biological substance collection method of the present disclosure have been described according to the foregoing embodiments and examples, but they are not limited to the foregoing embodiments and examples and may encompass various transformations, modifications, and improvements made to the various disclosed elements (including elements disclosed in the Claims, Description, and Drawings) within the scope of the invention and according to the fundamental technical idea of the invention. Further, various combinations, substitutions, and selections of the various disclosed elements are possible within the scope of the claims of the invention.

Further issues, objectives, and embodiments (including modifications) of the invention are revealed also from the entire disclosure of the invention including the Claims.

The numerical ranges disclosed herein are to be construed in such a manner that arbitrary numerical values and ranges falling within the disclosed ranges are treated as being concretely described herein, even where not specifically stated.

INDUSTRIAL APPLICABILITY

The stratum corneum-collecting adhesive composition, the stratum corneum-collecting instrument, the biological substance extraction kit, and the biological substance collection method according to the present disclosure can be used to check/examine the state of a customer's skin in, for example, a medical setting, a store selling cosmetics or external skin preparations, or the like.

REFERENCE SIGNS LIST

1: Adhesive composition;
1a: Hydrophilic component;
1b: Hydrophobic component;
2, 12: Support;
10, 20, 30: Stratum corneum-collecting instrument;
12a: Grip portion;
12b: Stratum corneum-collecting portion;
40, 43: Biological substance extraction kit;
41: Container;
41a: Opening;
44: Lid;
51: Stratum corneum;
52: Biological substance;
61: Extraction solvent.

The invention claimed is:

1. A stratum corneum-collecting adhesive composition comprising:
a hydrophobic component having adhesiveness;
a hydrophilic component that is present in a dispersed state in the hydrophobic component,
wherein a content by percentage of the hydrophilic component is from 15 to 50% by mass to a mass of the adhesive composition,
wherein a content by percentage of the hydrophobic component is from 50 to 85% by mass to the mass of the adhesive composition,
wherein the hydrophobic component contains a tackifier in an amount of from 10 to 50% by mass to the mass of the adhesive composition, a shape retention agent in an amount of from 5 to 50% by mass to the mass of the adhesive composition, and a softener in an amount of from 3 to 20% by mass to the mass of the adhesive composition, and
wherein the hydrophilic component contains at least one selected from the group consisting of water-soluble carboxymethyl cellulose and salts thereof, water-insoluble carboxymethyl cellulose and salts thereof, alginic acid and salts thereof, vinyl acetate/vinylpyrrolidone copolymer, polyvinylpyrrolidone, and polyvinylpolypyrrolidone.

2. The adhesive composition according to claim 1, wherein the tackifier contains at least one selected from the group consisting of rosin-based resins, terpene-based resins, and alicyclic hydrocarbon resins.

3. The adhesive composition according to claim 1, wherein the shape retention agent contains at least one selected from the group consisting of polyisobutylene, styrene/isoprene/styrene block copolymer, and styrene/butylene/styrene copolymer.

4. The adhesive composition according to claim 1, wherein the softener contains at least one selected from the group consisting of liquid paraffin, polybutene, lanolin, vegetable oils, carboxylic acid compounds, and ester compounds.

5. The adhesive composition according to claim 1, wherein the adhesive composition has a water absorption rate of 200% or less.

6. The adhesive composition according to claim 1, further comprising a hydrophilic nonionic surfactant in an amount of 5% by mass or less to the mass of the adhesive composition.

7. The adhesive composition according to claim 1, wherein the adhesive composition is for collecting a protein in the stratum corneum.

8. The adhesive composition according to claim 7, wherein the protein is at least one selected from the group consisting of SCCA1, SOD1, SOD2, IL-1ra, IL-1α, IL-1γ, MMP9, MMP2, AZGP1, cathepsins, S100 protein, VEGF, KLK-5, KLK-7, KLK-8, KLK-11, KLK-12, KLK-13, elafin, TACE, and CALML-5.

9. A stratum corneum-collecting instrument comprising:
the adhesive composition according to claim 1; and
a support having the adhesive composition provided to at least a portion thereof.

10. The stratum corneum-collecting instrument according to claim 9, wherein the support is a sheet.

11. The stratum corneum-collecting instrument according to claim 9, wherein:
the support includes a grip portion to be held by a user, and a stratum corneum-collecting portion extending from the grip portion; and
the adhesive composition is provided to at least a portion of the stratum corneum-collecting portion.

12. The stratum corneum-collecting instrument according to claim 11, wherein:
the stratum corneum-collecting portion has a columnar or rod-like shape; and
the adhesive composition is provided on a tip-end side which is on an opposite side from the grip portion.

13. A biological substance extraction kit comprising:
the stratum corneum-collecting instrument according to claim 9; and
a container that has an opening, and that is configured to receive the adhesive composition through the opening.

14. A biological substance extraction method comprising:
a collection step of attaching the adhesive composition according to claim 1 to the skin, and causing stratum corneum to adhere to the adhesive composition; and
an extraction step of bringing at least a portion of the adhesive composition, to which the stratum corneum has adhered, into contact with a solvent, and extracting a biological substance from the stratum corneum into the solvent.

15. The method according to claim 14, wherein, in the extraction step, the solvent is shaken while keeping the adhesive composition in contact with the solvent.

* * * * *